United States Patent [19]

Tran

[11] Patent Number: 5,019,723
[45] Date of Patent: May 28, 1991

[54] SELF-REGULATED THERAPEUTIC AGENT DELIVERY SYSTEM AND METHOD

[75] Inventor: Loi H. Tran, Wheaton, Ill.

[73] Assignee: Controlled Release Technologies, Inc., Chicago, Ill.

[21] Appl. No.: 416,109

[22] Filed: Oct. 2, 1989

Related U.S. Application Data

[62] Division of Ser. No. 129,159, Dec. 7, 1987, Pat. No. 4,871,352.

[51] Int. Cl.$^5$ ............................................. G11C 13/02
[52] U.S. Cl. ............................... 307/400; 210/500.38; 55/DIG. 39; 604/82
[58] Field of Search ................... 307/400; 210/500.37, 210/500.38; 55/155, DIG. 39

[56] References Cited

U.S. PATENT DOCUMENTS

| | | | |
|---|---|---|---|
| 3,660,736 | 5/1972 | Igarashi et al. | 307/400 |
| 3,793,715 | 2/1974 | Murayama et al. | 307/400 |
| 3,967,027 | 6/1976 | Igarashi et al. | 307/400 |
| 4,035,164 | 7/1977 | Taylor | 55/154 |
| 4,473,863 | 9/1984 | Magee | 307/400 |
| 4,513,049 | 4/1985 | Yamasaki et al. | 307/400 |
| 4,626,263 | 12/1986 | Inoue et al. | 307/400 |
| 4,720,345 | 1/1988 | Linder et al. | 210/500.37 |
| 4,789,504 | 12/1988 | Ohmori et al. | 307/400 |
| 4,874,659 | 10/1989 | Ando et al. | 307/400 |
| 4,889,636 | 12/1989 | Perry et al. | 210/500.37 |

FOREIGN PATENT DOCUMENTS

| | | | |
|---|---|---|---|
| 0050650 | 1/1975 | Japan | 307/400 |
| 0045097 | 4/1977 | Japan | 307/400 |
| 2060259 | 4/1981 | United Kingdom | 55/DIG. 39 |

OTHER PUBLICATIONS

Linder et al., "Persistent Electrical Polarization in Polyelectrolyte Membranes" J. of Phy. Chem., vol. 76, No. 23, 1972, pp. 3434-3445.
Metler et al., "Polyelectrolyte Membrane Electrets", J. of Phys. Chem., vol. 80, No. 12, 1976, pp. 1387-1388.

*Primary Examiner*—C. Fred Rosenbaum
*Assistant Examiner*—Sharon Rose
*Attorney, Agent, or Firm*—Olson & Hierl

[57] ABSTRACT

A self-regulated system and method for controllably administering a therapeutic agent to a patient is disclosed. A therapeutic agent is driven by unidirectional electrostatic diffusion across a rate-controlling electret membrane. The diffused therapeutic agent is then delivered to a patient. The preparation of the electret membrane and therapeutic agent delivery apparatus are also disclosed.

5 Claims, 5 Drawing Sheets

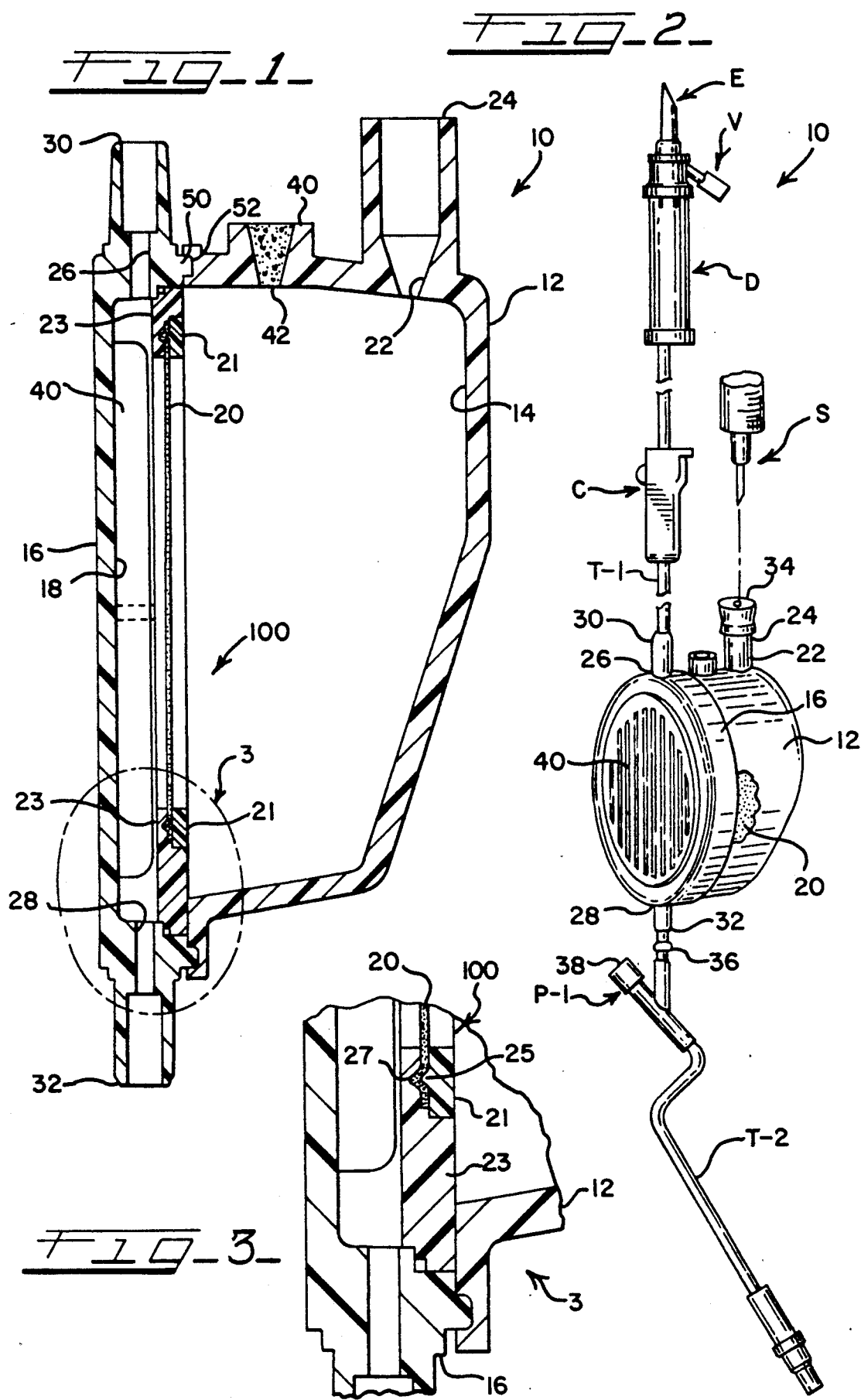

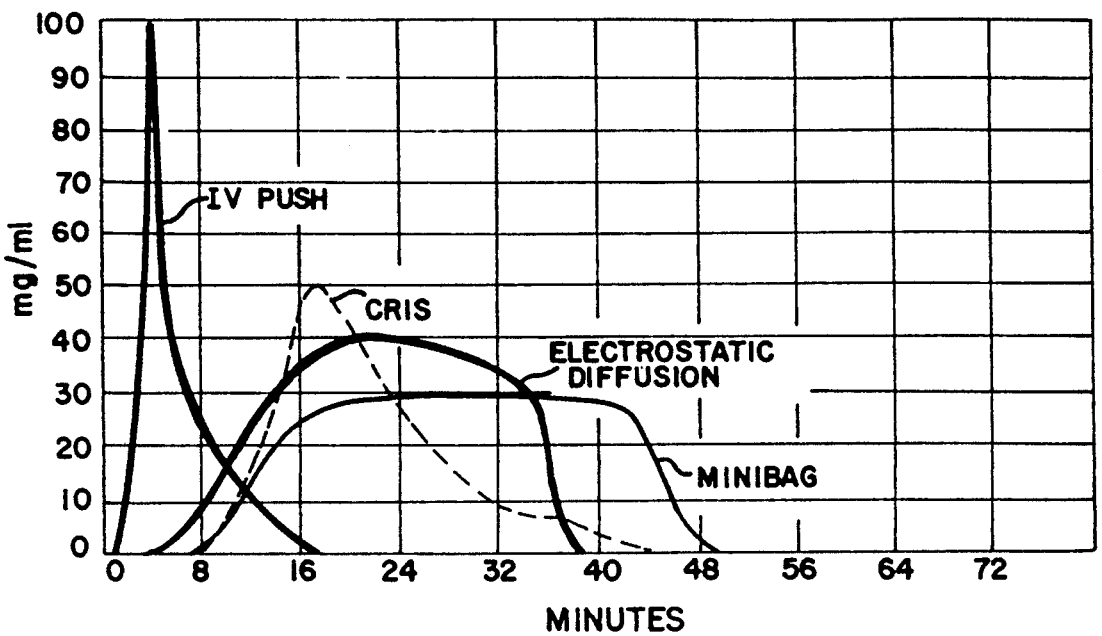
FIG-8-
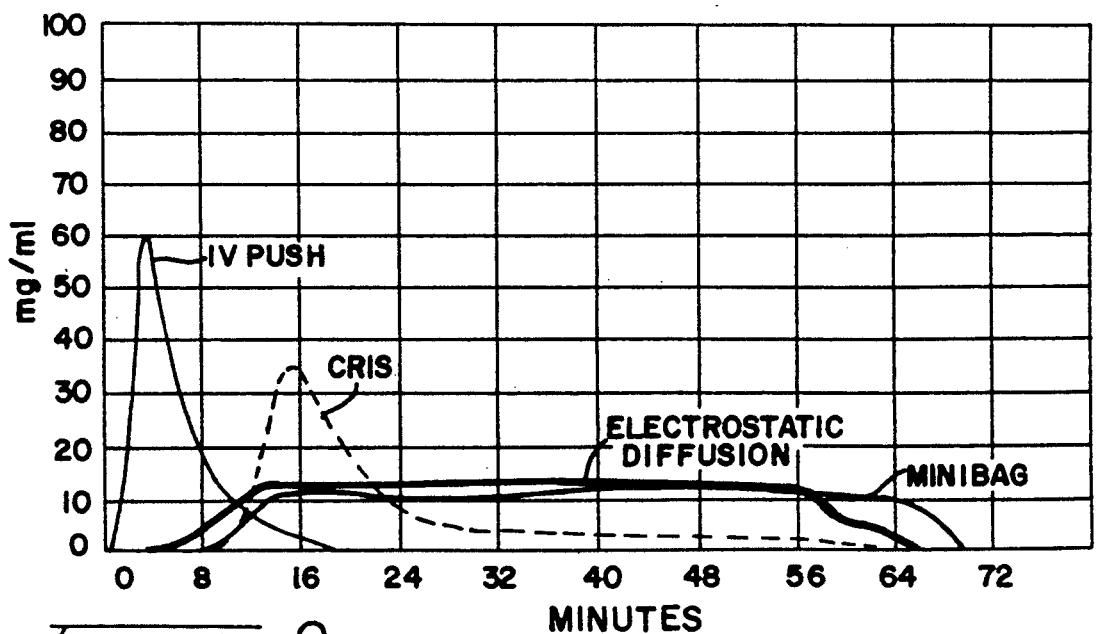
FIG-9-

SELF-REGULATED THERAPEUTIC AGENT DELIVERY SYSTEM AND METHOD

This is a division of application Ser. No. 129,159, filed Dec. 7, 1987, now U.S. Pat. No. 4,871,352.

TECHNICAL FIELD OF THE INVENTION

The present invention relates to systems and methods for administering a therapeutic agent to a patient by means of an electrokinetic potential across the surface of a membrane.

BACKGROUND OF THE INVENTION

It is quite common to administer a predetermined dosage of a drug to a patient over time by first diluting the drug in a liquid vehicle such as saline. Generally, the drug is mixed with the liquid vehicle, and the resulting solution is then administered intravenously to the patient. However, such systems require that the drug be carefully mixed into the solution for proper delivery.

To simplify the administration and storage of certain drugs, they are provided in a crystal form. The crystals are then mixed with a physiologically tolerable solution until the crystals dissolve. Unfortunately, unless care is taken to be sure the crystals are completely dissolved before the mixture is administered to the patient, adverse effects can result.

Various proposals have been made over time to mix a drug into a solution such as saline before it is administered to the patient. One such device is the CRIS system sold by IVAC of San Diego, Calif. In that system, the saline infuses into a container holding the drug solution. The mixture of the saline and drug is then delivered to the patient. Unfortunately, while the CRIS system allows diluted drug to be administered, it provides the drug at a changing dilution over time. As the system operates, the dilution of the drug increases as more and more drug is "washed out" of the container.

Other devices have been proposed which allow the drug to leach through a membrane to be delivered into a stream of saline over time. Unfortunately, there is no control over the leaching process and the dilution of the drug decreases over time. In addition, should the flow of saline be stopped, the drug will continue to leach into the saline. If the flow is then restarted, a concentrated and possibly dangerous flow of saline and drug will be delivered to the patient.

Accordingly what is needed is a system which provides a relatively constant dilution of drug to the patient. Such a system should provide a barrier against possible infusion of crystals from the preparation of the drug or possible bacteria which may be accidentally introduced into the drug solution. In addition, such a system should inherently prevent an excess of concentration of drug from being delivered to the patient. The self-regulated therapeutic agent delivery system, apparatus and method of the present invention meets these desires.

SUMMARY OF THE INVENTION

The present invention is a self-regulated system and method for delivering one or more therapeutic agents to a patient by driving a therapeutic agent across a semipermeable porous membrane having an ionically charged surface. In one embodiment, a therapeutic agent is unidirectionally driven through a rate-controlling electret membrane by an electrokinetic potential across the surface of the membrane resulting in electrostatic diffusion.

The rate-controlling electret membrane is preferably a polarized polyelectrolyte membrane made of a polyelectrolyte salt and a polar permselective polymer matrix. The permselective membrane is preferably a microporous polymeric film-forming material that has its surface modified so that it is ionically charged to be ion-selective.

The term "electret" refers to that phenomenon where a material is electrically polarized such that it retains a residual dielectric field. This residual field stores energy that can be discharged. The primary function of the polyelectrolyte in such a polymer matrix is believed to serve as an electrical power storage device for the rate-controlling membrane.

Surprisingly, an electret has been found in which the stored energy is discharged by the movement of liquid ionic species on the surface of the membrane. Prior electret systems disclosed by the art require either elevated temperature, ultraviolet light, a magnetic field or gamma radiation to make the stored energy available.

A preferred electret membrane is formed by impregnating a polyanion in a porous, semipermeable, hydrophilic polymer matrix. A preferred polymer matrix has a porosity of about 0.01 micrometers. A particularly preferred polymer matrix is a modified Nylon 66 film having about 50 percent amine and abour 50 percent carboxyl functional groups on its surface. A particularly preferred polyanion is sodium polystyrene sulfonate of about 2 million to about 4 million average molecular weight.

Surprisingly, a rate-controlling membrane of this invention is formed of electret material by relatively simple immersion impregnation technique under ambient atmospheric conditions without electrical polarizers.

A therapeutic agent delivery system of this invention generally comprises a first housing defining a donor chamber and a second housing defining a receiving chamber. The chambers are divided by the rate-controlling electret membrane of this invention. The donor chamber is adapted to retain a therapeutic agent and the receiving chamber has an inlet and an outlet and is adapted to receive a physiologically tolerable liquid.

As the liquid in the receiving chamber flows from the inlet to the outlet, it changes the electrokinetic potential across the surface of the electret membrane. This change causes a unidirectional movement of dielectric charges such that ionized therapeutic agent in contact with the opposite donor side of the membrane migrates across in response to balance the dielectric charge makeup of the membrane. In effect, the electret membrane functions as an electrostatic valve.

Suitable therapeutic agents include active agents such as drugs or hormones, or active agents coupled to an appropriate carrier. Either the active agent or the carrier is in an ionic form such as a pharmaceutically acceptable salt. For example, such a salt can be represented by the formula $RY^+X^-$ wherein $RY^+$ includes a cationic (positively charged) group such as $RNH^+3$, and $X^-$ is an anionic (negatively charged) group such as $Cl^-$ or $Br^-$. For example, a drug that is a hydrochloride salt has a positive charge when ionized.

In one embodiment, the donor chamber is in fluid communication with an inlet port and a vent including an air permeable hydrophobic sealing means. The vent is positioned such that it is free from contact with the therapeutic agent retained in the donor chamber.

After the therapeutic agent enters the receiving chamber by electrostatic diffusion, it can be delivered to a patient by an appropriate delivery means. One preferred form of delivery is to pass a physiologically tolerable aqueous liquid vehicle containing a polar species, such as sodium chloride, or a non-polar species, such as dextrose, through the receiving chamber to mix with the diffused therapeutic agent and deliver the mixture to the patient intravenously.

In a preferred embodiment, the receiving chamber is positioned in generally parallel vertical relationship to the donor chamber. The electret membrane is secured between the first housing defining the donor chamber and the second housing defining the receiving chamber by means of an interlocking ridge and groove around the periphery of the membrane.

In a preferred method aspect, the self-regulated controlled release of therapeutic agent is accomplished by placing at least one ionized therapeutic agent in the donor chamber and in contact with the electret membrane. An ionized physiologically tolerable liquid is received in the receiving chamber and in contact with the electret membrane. Electrostatic diffusion of therapeutic agent is intermittently or continuously delivered from the donor chamber to the receiving chamber by regulating the flow movement of the liquid in the receiving chamber. The diffused therapeutic agent is delivered to a patient.

Surprisingly, when liquid is present in only one of either the donor chamber or the receiving chamber, no electrostatic diffusion takes place across the electret membrane to the empty chamber.

In this embodiment, therefore, therapeutic agent can be intermittently or continuously delivered from the donor chamber, because the device is self-pumping. Additionally, the therapeutic agent is unidirectionally diffused from the donor chamber to the receiving chamber. Because this movement is in response to a change in the electrokinetic potential across the surface of the electret membrane in contact with a moving film of liquid in the receiving chamber, the rate and amount at which diffused therapeutic agent is delivered to a patient can be easily and manually controlled. The rate and amount of delivery through the rate-controlling membrane is a function of the capacity of electric charges stored on the surface of the electret from the polyelectrolyte, and of the surface area, the thickness and the porosity of the polymer matrix.

In one aspect, the electret membrane serves as a porous filter for particulates and bacteria and as a barrier over which the ionic therapeutic species have to pass in order to go from one side of the membrane to the other side. Surprisingly, even though some of these ionic species or charged particles are smaller in size than the pores of the electret membrane, they do not cross the membrane unless the electrokinetic potential on the membrane is changed by flowing liquid in contact with the receiving side. In another aspect, the membrane functions as an electrostatic valve.

Because the electrokinetic potential of the rate-controlling membrane is a function of the surface area on both sides of the membrane in contact with ionized or electrolytic media, unidirectional flow of ionized therapeutic liquid by gravity is achieved through the membrane to the receiving chamber. Thus, the delivery system is self-regulating and self-pumping. In effect, therapeutic agent is continuously delivered otherwise uninterrupted by external mechanical failures. Where such uninterrupted delivery is desired, this device has an inherent advantage because it can be used under emergency conditions, such as in a power failure or where, mechanical controlling means are generally unavailable or undesired.

Another benefit of a manual therapeutic agent delivery system of this invention utilizing electrodiffusion is that it can be employed as part of all of a portable and disposable patient administration assembly. Because the device is self-pumping and self-limiting, it can be used to infuse fixed volumes of therapeutic agents over prolonged administration times without interfering with the administration of supplementary medications.

Numerous other advantages and features of the present invention will become readily apparent to those skilled in the art from the following detailed description of the preferred embodiments of the invention, the drawings, and the claims.

BRIEF DESCRIPTION OF THE DRAWINGS

FIG. 1 is an elevational view, in section, of a preferred disc-shaped embodiment of the present invention provided with a rate-controlling electret membrane;

FIG. 2 is a perspective view of the embodiment of FIG. 1 generally positioned as part of a patient administration assembly for delivery of therapeutic agent to a patient;

FIG. 3 is an enlarged view of the area enclosed by line 3 of the embodiment of FIG. 1;

FIGS. 8-13 are graphical representations of controlled drug delivery of a therapeutic agent from a device similar to the embodiments of FIGS. 1 and 2.

DETAILED DESCRIPTION OF THE PREFERRED EMBODIMENTS

Figure 4:
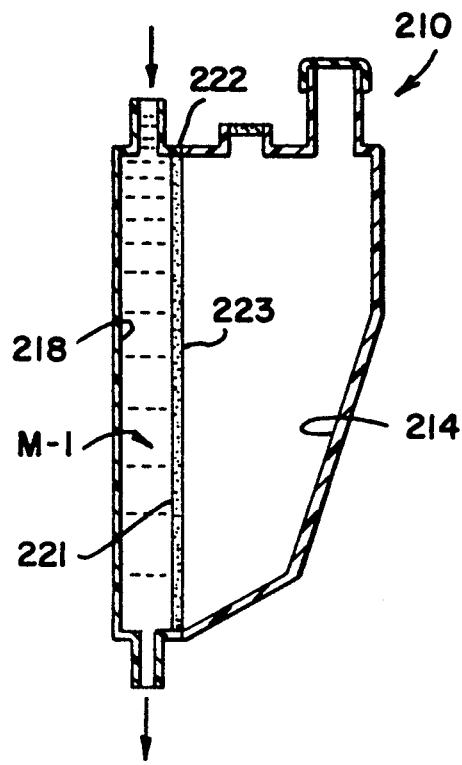
FIGS. 4-7 are schematic representations of the principles of this invention in delivering therapeutic agent by electrostatic diffusion.

While this invention can be embodied in many different forms, there are shown in the drawings and described in detail, preferred embodiments of the present invention. The present disclosure is an exemplification of the principles of the invention and is not intended to limit the invention to the embodiments illustrated.

The present invention is a method and system for administering one or more therapeutic agents to a patient. The therapeutic agent can be almost any active agent, such as a drug or hormone, which can exist in an ionized form. Alternatively the therapeutic agent can be an active agent coupled to a carrier that is ionizable, as disclosed by Tran in patent application Ser. No. 679,128, filed Dec. 6, 1984, now assigned U.S. Pat. No. 4,715,850, the disclosures of which are incorporated by reference.

A device of this invention defines a donor chamber and a receiving chamber separated by a rate-controlling electret membrane. The donor chamber is adapted to retain a therapeutic agent in ionized form, and the receiving chamber has an inlet and outlet adapted to receive physiologically tolerable liquid for flow communication from the inlet to the outlet.

To deliver therapeutic agent under the principles of this invention, the therapeutic agent is placed within the donor chamber in its ionic form. The donor chamber is defined in part by the rate-controlling electret membrane which is made of a material having an electrokinetic potential that provides an ionic surface. The electret material is comprised of a polyelectrolyte and a polar polymer matrix.

The phenomenon of electret membrane formation has been reported to involve polarization and seems to decay by mechanisms of dielectric relaxation. See generally Miller, *Energy*, 4, 307 (1979), Linder and Miller, *J. Electrochem. Soc.*, 120, 498 (1973), Miller and Mayoral, *J. Phys. Chem.*, 80, 1387 (1976) and Bornzin and Miller, *J. Electrochem. Soc*, 125, 409 (1978). In contrast to a chemical battery in which the energy stored is made available by connecting the electrodes to an external circuit, an electret system requires an additional step to make the energy available, such as raising the external temperatures leading to the electret system or using ultraviolet light, etc.

In this invention, semipermeable electret membranes are prepared by immersing a prefabricated porous polymer matrix in a bath of polyelectrolyte solution and elevating the temperature of the bath up to preferably between 63 to about 67 degrees C., optimally about 65 degrees C., and thermostatically maintaining this temperature for about 50 minutes to one hour. The electret membrane is then removed and dried preferably under a laminar flow of filtered air at ambient atmospheric conditions overnight.

The semipermeable electret membrane is permeable with respect to the charge of the ionized therapeutic agent, but is substantially impermeable to an oppositely charged ion. Polymeric matrix materials suitable as solid supports can also be membranes as commonly understood in the art but are not electret membrane materials as supplied. The membrane is preferably made of a microporous, inherently hydrophilic matrix film. The term "microporous" means a material having a pore size less than about 0.22 micrometers, preferably about 0.01 micrometers, as the solid support for the polyelectrolyte. The term "hydrophilic" means a matrix that naturally adsorbs or absorbs water.

A variety of polymeric matrices may be used to prepare an electret membrane suitable for use in a device of this invention. A relatively extensive listing and discussion of such polymer membranes is found in U.S. Pat. No. 4,673,504, incorporated herein by reference. Such materials may exhibit ion selectivity based on differentials in porosity, as well as surface charge. In such an instance, a polymeric material already bearing the desired surface charge is fabricated into the shape of the membrane and then formed into an electret. Alternatively a pre-fabricated membrane may be subsequently treated to modify its surface charge prior to forming an electret. Suitable matrix materials may be selected from positively charged (cationic) and negatively charged (anionic) polymers, as well as matrix materials possessing both a positive and a negative charge.

A preferred microporous matrix is one produced from nylon film having its ionic surface modified with amine functional groups and carboxyl functional groups. The term nylon includes film forming polyamide resin and copolymers and terpolymers thereof. A particularly preferred nylon is Nylon 66, a copolymer of hexamethylenediamine and adipic acid.

A particularly preferred electret membrane was made using a commercial polymer matrix comprising a modified Nylon 66 membrane having a protein-like surface populated by 50 percent amine functional groups and 50 percent carboxyl functional groups sold by Pall, Biosupport Division, of New York under the trademark Ultipor N66. According to the manufacturer, this membrane is isoelectric at pH 6 and can selectively have a positive zeta potential at a pH<6 and a negative zeta potential at pH>6.

A suitable electret formed using this polymer matrix was prepared by the method described above. The matrix had a porosity of about 0.01 micrometers and was fabricated in the shape of a disc about 1.5-1.75 inches (3.8 to 4.4 cm.) in diameter. This disc was impregnated with a polyelectrolyte solution of 0.09 Molar PSSNa obtained from Dow Chemical Company under the trade designation DOW SA-1291.1. The polyelectrolyte had an average molecular weight of about two million to about four million. The resulting electret membrane had an ion exchange capacity averaging about 2.0 milliequivalents per dry gram weight.

Exemplary negatively charged polymer matrix materials for the membrane include anionic polymers, such as perfluorosulfonic acid polymers, carboxylic acid polymers such as poly(sodium methacrylate), and phosphoric acid polymers, such as poly(vinyl sodium phosphonate), polyacrylic acid and polyethylene terephthalate. One particularly preferred polymer is a perfluorosulfonic acid polymer having internal sulfonic acid groups sold by Cole Parmer of Chicago, Ill. as part of its Spectra/Por family of membranes. Another particularly preferred material is nylon, especially a Nylon 66, modified to provide a high concentration of carboxyl functional groups at the surface of the material's pores. Such a material is sold by Pall, BioSupport Division, of New York under the trademark Carboxydyne. The manufacturer of the Pall Carboxydne membrane support states that this material has a negative zeta potential in both basic and acidic solutions. Another suitable material includes a cation exchange membrane sold by Asahi Glass & Co. under the trademark Selemion CSV.

An exemplary positively charged matrix is Nylon 66 modified by the addition of quaternary ammonium groups sold by Pall, Biosupport Division, of New York under the trademark N66 Posidyne. According to the manufacturer, a high concentration of these cationic functional groups at the pore surface of the material produces a positive zeta potential in both acidic and basic solutions over a pH range of 3-10.

Exemplary polymeric materials possessing a combined positive and negative charge may comprise insoluble polyelectrolyte complexes or polysalts, such as a copolymer of the polyanion, poly(sodium styrene sulfonate) and the polycation, poly(vinylbenzyltrimethylammonium chloride).

The foregoing materials are illustrative of suitable polymers matrices that may be used in preparing polyectrolyte electret membranes for use in the device embodiments of this invention. The invention is not limited to these specific materials, but rather encompasses those materials possessing the requisite porosity and charge capability for practicing the principles of this invention. Another criteria is that the polymer matrix withstand sterilization techniques, especially gamma ray radiation.

Suitable polyelectrolytes for preparing a membrane of this invention include polyanions, such as sodium polystyrene sulfonate (PSSNa), sodium polypropylene sulfonate, sodium ethylene sulfonate and the like. The criteria for selecting the polyelectrolyte is limited only by its approval for use in devices for delivering therapeutic agents to human being. For this purpose, the material used is preferably of pharmaceutical grade and meets the standards of the United States Pharmacopeia (U.S.P.). PSSNa of U.S.P. grade is particularly preferred.

The rate-controlling mechanism of the electret membrane of this invention is not fully understood. It is believed that the surface of the membrane has a lamina of polyelectrolyte which provides a double layer of positive and negative charges on both the donor side and the receiving side of the membrane. It is further believed that unidirectional movement of dielectric charges from the donor side to the receiving side of the membrane is produced in response to hydrogen bond and dielectric charge interactions between the water molecules and polar species, such as sodium chloride in saline or non polar species, such as dextrose in dextrose solution, flowing in contact with the receiving side of the membrane.

Electrostatic diffusion of the therapeutic agent is achieved when the electrostatic potential is changed on the surface of the receiving side of the rate-controlling electret membrane, i.e., in fluid communication with the receiving chamber. The electrostatic potential is changed by contact with flowing medium, such as saline, received in the receiving chamber. When ionized therapeutic agent is simultaneously in contact with the surface of the donor side of the membrane, ionized therapeutic agent unidirectionally diffuses from the donor chamber and is driven through the membrane for delivery to the patient.

Referring to FIG. 1, a disc-shaped device 10 suitable for electrodiffusion in the above described manner is shown. Device 10 includes a first housing 12 which defines donor chamber 14 and a second housing 16 which defines receiving chamber 18. The device also includes a delivery rate-controlling membrane 20 made of an electret material. As shown, the donor chamber 14 is separated from the receiving chamber 18 by the rate-controlling electret membrane 20.

In this embodiment, the periphery of the membrane 20 is secured between a first securing means 21 and a second securing means 23 and is sonically welded to form a bonded membrane assembly 100. The securing means is preferably in the form of a washer or gasket.

The bonded membrane assembly 100 is then captured between the housings by the interlocking ridge 50 defined by the second housing 16 which is received in a groove 52 defined by the first housing 12. The ridge 50 is made about 0.020 inches (0.5 millimeters) high and the groove 52 about 0.012 inches (0.3 millimeters) deep. The housings are pressed together with the membrane assembly 100 captured in between and held by the ridge and groove, when the housing are connected. The housing are sealed against leakage by being sonically welded together. The amount of energy used to sonically weld the housing together depends on the materials chosen. Alternatively, the periphery of the membrane can be captured directly between the ridge and groove of the housings.

The donor chamber 14 is adapted to hold the therapeutic agent while the receiving chamber 18 is adapted to receive the therapeutic agent from the donor chamber 14 through the membrane 20. In this embodiment, the donor chamber 14 is further provided with a vent 40 including a sealing means 42. Alternatively, the donor chamber can be non-vented and instead made of a collapsible body material.

The vent is preferably positioned free of contact with therapeutic agent retained in the donor chamber to avoid blocking air escape. Preferably, the vent is positioned a point above the level of liquid therapeutic agent in the donor chamber, but is not so limited. The vent can be positioned on a lateral wall of the device so long as its venting action is not blocked by the liquid retained in the donor chamber.

The sealing means 42 is preferably composed of air-permeable, liquid impermeable hydrophobic material, such as silicone elastomers consisting of dimethyl and methylvinyl siloxane copolymers commercially available from Dow Chemical under the trademark Silastic, polyurethane rubber and the like. Other suitable membranes include Teflon TFE membranes (trademarks of duPont de Nemours & Co.), a styrene ethylene/butylene, styrene block copolymer with polydimethylsiloxane available under the trademark C-Flex from Concept Polymer Technologies and a polytetrafluoroethylene available under the trademark Gore-Tex from W. L. Gore & Associates, Inc.

In this embodiment, the first or donor housing 12 is also provided with the inlet port 22 having an introduction means 24 in the form of a standard luer-type fitting for connection with conventional therapeutic agent reservoirs, such as a syringe, medicine vial or infusion tube. Similarly, the second or receiving housing 16 includes an inlet 26 and an outlet 28 in fluid communication with the receiving chamber 18. These are provided, respectively, with an inlet port 30 and an outlet port 32 also in the form of standard luer-type fittings for easy connection to conventional flexible tubing.

As shown, the lower portion of the donor chamber is preferably angularly sloped towards the receiving chamber. When therapeutic agent is placed in the donor chamber, this slope maximizes contact of therapeutic agent with the membrane as the volume in the chamber decreases. In a preferred embodiment, the internal face of the receiving housing 16 includes laminar flow ridges 40 to reduce turbulence within the receiving chamber 18.

The device 10 as shown has the donor chamber 14 separated by the rate controlling membrane 20 from the receiving chamber 18 in generally vertical parallel relationship. The device 10 can be held stationary in either a vertical position as shown in FIG. 1 so that the donor chamber 14 remains generally parallel to the receiving chamber 18. Alternatively, the device 10 can be cradled in a stationary horizontal position with the receiving chamber 18 held in the palm of one hand while introducing the therapeutic agent to the donor chamber 14.

Turning now to FIG. 2, the device 10 is pictured generally positioned as part of a patient administration assembly for delivery of a therapeutic agent by connection to a patient administration device.

In this embodiment, the donor housing inlet port 22 is further provided with an introduction means 24 including a puncturable sealing means 34 for convenience in introducing a therapeutic agent to the donor chamber 14, as by a conventional hypodermic syringe and needle assembly S. Therapeutic agent can be introduced by holding the device 10 stationary with one hand while piercing the sealing means 34 with the needle portion of the hypodermic syringe and needle assembly S held in the other hand.

Physiologically tolerable liquid is received from an infusion source (not shown) by connecting flexible tubing T-1, such as intravenous tubing, to the inlet port 30 and is allowed to flow through the receiving chamber 18. Therapeutic agent migrates by electrostatic diffusion across the membrane 20 (shown in cutaway section) from the donor chamber 14 to the receiving chamber 18 and mixes with the liquid. This mixture is then delivered to a patient by delivery means such as flexible tubing T-2 connected to the outlet port 32 leading to a conventional patient administration device (not shown), such as an indwelling vascular catheter or needle.

The flow of the liquid to receiving chamber 18 can also be controlled manually as shown in FIG. 2 by a clamping means C, such as a roller clamp, slideably positioned on the tubing T-1 between the inlet 26 of the receiving chamber and the infusion source. Additionally, the influent flow of liquid to the receiving chamber can be controlled in a generally conventional manner by adjusting the flow rate from the infusion source into a drip chamber D. As shown in FIG. 2, the drip chamber D can be further adapted as by the spiked end E for releasably mating with the infusion source and can be appropriately vented with the vent means V.

The effluent flow of liquid from the receiving chamber 18 to the patient can be manually controlled or interrupted in-line by including a valve means 36, such as a slide clamp or three-way valve, positioned between the outlet port 32 and the patient.

For delivery of therapeutic agent received in the receiving chamber by electrostatic diffusion, the tubing T-2 preferably further includes an injection port P1 having sealing means 38 positioned for in-line communication between the valve 36 and the patient administration device. This permits supplementary therapeutic agent to be injected as desired without interfering with the electrostatic diffusion taking place in the device 10.

FIG. 3 illustrates an enlarged view of the periphery of the membrane assembly 100 taken in the area generally enclosed by line 3 of FIG. 1. The membrane assembly 100 is prefabricated by positioning the membrane 20 between a first securing means 21 having a generally rounded ridge 25 and a second securing means 23 having a generally rounded groove 27. The generally rounded shape of the ridge 25 and groove 27 permit the membrane 20 to be captured without cutting or otherwise damaging the membrane. The membrane assembly 100 is prepared by a shear join sonic weld connecting the membrane 20 and securing means 21, 23 together. The membrane 20 is preferably captured between the first and second housing means with the first and second securing means also in contact with each other. A preferred method of welding utilizes an ultrasonic welding machine with the ultrasonic energy director placed at a distance of about 0.020 inches. A suitable welding machine is available from Bramson Sonic Power Co., division of Bramson Ultrasonics Corporation, Danbury, Conn.

After the membrane assembly 100 is prepared, it is positioned between the first housing 12 and the second housing 16, and then sealed around the edges against leakage by sonic welding. By preparing a membrane assembly in this manner, the integrity of the membrane remains intact when it is captured between the housings and no undesirable leakage occurs.

Another advantage is that the securing means can be selected in the form of a washer or gasket or disc each defining an opening equal or dissimilar size to vary the dimension of the exposed surface area of the membrane in communication with either the donor side or the receiving side of the membrane. The same housing design can then be used for many different devices with the size of the opening in the membrane assembly chosen as desired.

The housings of this invention can be made of any suitable medical grade material. Such materials include glass, polypropylene, polyethylene, polycarbonate, acrylate and polystyrene and are preferably sterilizable and disposable for one time use. The housings are preferably composed of an acrylic material, such as PLEXIGLAS DRG-100 sold under this trademark by Rohm & Haas Co. of Pennsylvania. Another preferred material has the trade designation CRYOLITE and is sold under the trademark G20 HIFLO by Cryo Industries of Connecticut. These materials are approved by the Food and Drug Administration for medical use and can be sterilized by steam autoclave, ethylene oxide or by gamma-ray radiation.

Figure 5:
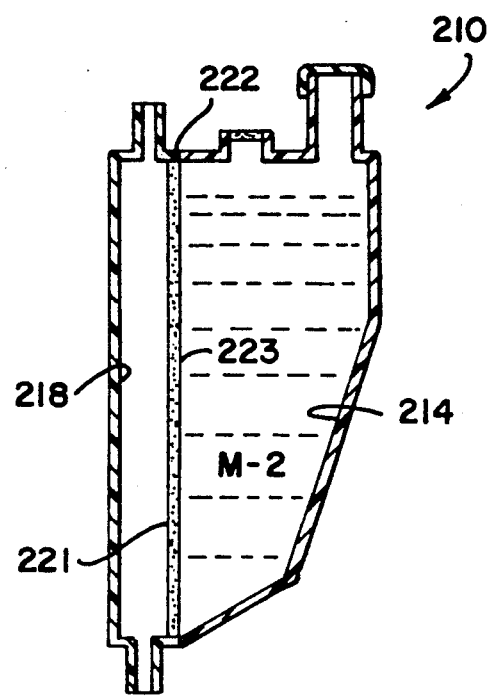

The principles of this invention are illustrated generally by the schematic representation in the device 210 shown in FIGS. 4–7. No electrostatic diffusion occurs when either the donor chamber 214 or the receiving chamber 218 is empty, as shown in FIGS. 4 and 5 respectively. Thus, when no therapeutic agent delivery is desired, either the receiving side 221 or the donor side 223 of the electret membrane 222 is kept from contacting liquid M-1 or therapeutic agent M-2. This can be accomplished in one aspect by keeping the donor surface side 223 of the membrane dry, as by keeping the donor chamber 214 empty.

Figure 6:
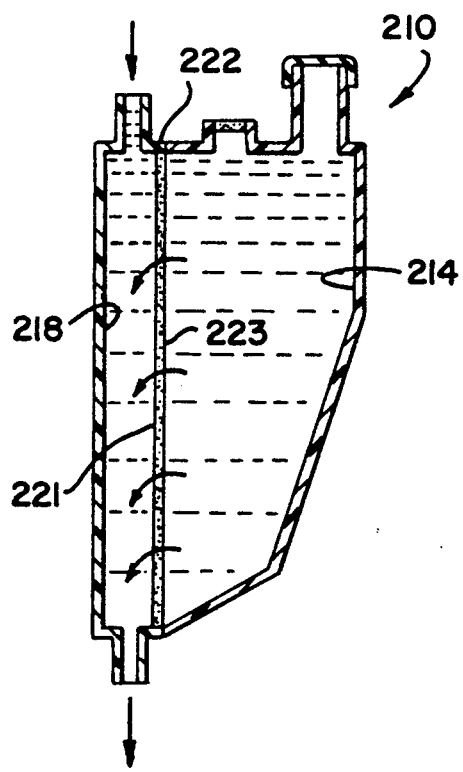
Figure 7:
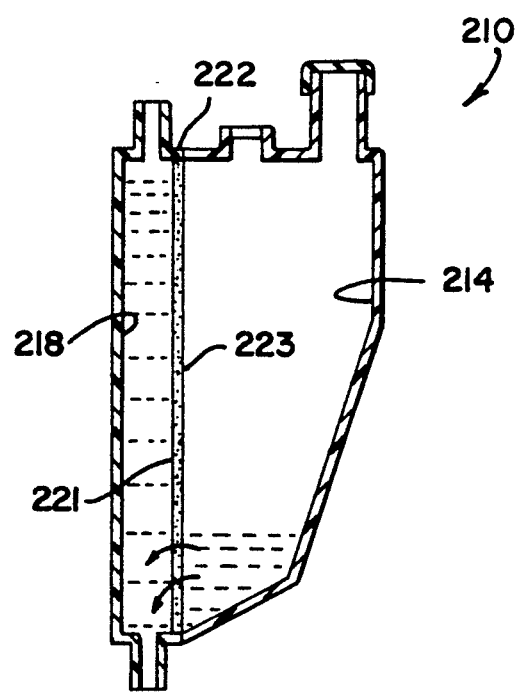

As shown in FIGS. 6 and 7, electrostatic diffusion takes place when both sides of the membrane surface 221, 223 are in contact with liquid media and there is a flow through the receiving chamber 218. Diffusion is unidirectional from the donor chamber 214 to the receiving chamber 218. In these representations, the donor chamber 214 and the receiving chamber 218 are vertically parallel and electrostatic diffusion from the donor chamber takes place from the surface area of the donor side 223 of the membrane 222 in contact with the therapeutic agent M-2 in response to flow contact of liquid M-1 with the receiving surface side 221 of the membrane.

It has been surprisingly found that as the meniscus of liquid therapeutic agent M-2 present in the donor chamber 214 changes, the amount of therapeutic agent that crosses remains substantially unchanged thereby making the membrane delivery rate-controlling and the device self-regulating.

Thus, using an electrostatic device of this invention, a predetermined continuous or intermittent dosage protocol can be controlled for certain families of injectable drugs, such as antibiotics, antieoplastic agents, cardiovascular drugs, analgesics and antipyretics. For example, in typical intermittent administration of an antibiotic, 500 milligrams or one gram of antibiotic drug is administered over a period of about 30 to 60 minutes. Using a device incorporating the electrostatic diffusion principles of this invention, such drugs can be infused in a fixed volume of about 10 to about 20 milliliters over a period of about 20 minutes to about 3 hours.

In another embodiment, a removable drug reservoir can also be provided in fluid communication with the donor chamber. If desired the drug reservoir can be elevated relative to the donor chamber so that gravity continuously drives the therapeutic agent into the donor chamber to replace that agent which has passed through the semipermeable membrane and has been administered to the patient. In this instance, however, the level of the volume introduced into the donor chamber should be monitored to avoid blocking the vent.

Alternatively more than one therapeutic agent can be introduced to the donor chamber as long as the combination does not deactivate their potency. In this embodiment, the rate at which each therapeutic agent present in the donor chamber diffuses across the membrane can be either the same or different, as desired. For example both Lidocaine and Nafcilin can be placed in the donor chamber together and the respective delivery rates will be similar. Until now, the delivery of multiple therapeutic agents from a single chamber was not generally possible.

A preferred disc-shaped device of this invention can be configured to have an overall dimensional size of about 2 inches diameter and 1.75 inches thick and a net weight of about 16.8 grams. Preferably the matrix of the membrane is inherently hydrophilic and does not have any measurable effect on the surface tension of water, alcohol or other liquid passed through it and should not affect the pH value of the therapeutic agent or change its composition.

The volume capacity for the receiving chamber is preferably about 3 to about 5 milliliters, most preferably 3.5 milliliters. The volume capacity of the donor chamber is preferably about 4 to 5 times greater than that of the receiving chamber.

For use, the device is first primed by passing primary liquid fluid, such as saline or dextrose, through the receiving chamber to purge it of air while the donor chamber is empty. In one preferred embodiment at least one therapeutic agent can be introduced to the donor chamber by means of a vented pre-filled syringe, such as Add-Vent sold by Quest, Inc. and by Becton Dickinson, Inc. or Vented-Plus sold by the assignee of this invention.

The therapeutic agent is preferably an ionizable drug that can be supplied as a pharmaceutically acceptable salt. The term "pharmaceutically acceptable salt" refers to the non-toxic alkali metal, alkaline earth metal and ammonium salts commonly used in the pharmaceutical industry including the sodium, potassium, lithium, calcium, magnesium, and ammonium salts and the like which are prepared by methods well known in the art. The term also includes non-toxic acid addition salts which are generally prepared by reacting the compounds of this invention with a suitable organic or inorganic acid. Representative salts include the hydrochloride, hydrobromide, sulfate, bisulfate, sulfonate, acetate, oxalate, valerate, oleate, laurate, borate, benzoate, lactate, phosphate, tosylate, citrate, barbital, maleate, fumarate, succinate, tartrate, and the like.

A wide range of drugs are available as pharmaceutically acceptable salts, and particularly as sodium salts. These include the sodium salts of cephalosporic acid, sodium salts of beta-lactam antibiotics, sodium salts of penicillin. Drugs available as hydrochloride and as sulfate salts include aminophylline hydrochloride, doxorubicin hydrochloride, clonidine hydrochloride, dopamine hydrochloride, lidocaine hydrochloride, naloxone hydrochloride, nalorphine hydrochloride, morphine hydrochloride, morphine sulfate U.S.P., and the sulfate salts of aminoglycosides.

Where the drug or hormone cannot be placed in an ionic form, or it is not desirable to place the drug or hormone in an ionic form, the therapeutic agent can include the drug or hormone coupled to an appropriate physiologically tolerable carrier which does have an ionic form. This is particularly useful for hormones such as insulin. Such appropriate carriers are disclosed in the patent application Ser. No. 679,128 corresponding to U.S. Pat. No. 4,715,850 mentioned above which is incorporated herein by reference.

EXAMPLE 1

This example illustrates the method of preparing a rate-controlling electret membrane suitable for use in a therapeutic agent delivery device of this invention.

A polymeric matrix of hydrophilic modified Nylon 66 was selected for use as the solid support and obtained from Pall Biosupport Division under the trade designation, Ultipor N66. This polymer matrix is described in the manufacturer's sales literature as having a protein-like surface populated by 50 percent amine functional groups and 50 percent carboxyl functional groups. These functional groups provide a matrix surface that is isoelectric at pH 6 and can have a positive zeta potential at $pH < 6$ and a negative potential at $pH > 6$.

The polymer matrix had a porosity of about 0.01 micrometers and a thickness of about 0.02 inches (about 1.5 millimeters). The polymer matrix was sized in the shape of a disc about 47 millimeters in diameter.

The polyanion, sodium polystyrene sulfonate, was selected as the polyelectrolyte, and obtained in a U.S.P. grade as a 0.09 Molar solution from Dow Chemical Company under the trade designation Dow SA-129.1.

The electret membrane was prepared by impregnating the polymer matrix with polyelectrolyte. This was accomplished by immersing the disc in the polyelectrolyte solution, raising the temperature of the solution to between about 62 to 67 degrees C. and thermostatically maintaining this temperature within 2 degrees of 65 degrees for a period of about 50 minutes to one hour. This impregnating solution was continuously stirred during this period.

The electret membrane was removed from the solution and allowed to dry under a filtered stream of air at ambient room temperature conditions overnight. The ion exchange capacity of the membrane was determined as averaging about 2.05 milliequivalents per dry gram basis.

A disc-shaped device generally similar to the embodiment shown in FIG. 2 was prepared. The external dimensions of the device were approximately one-inch thick and one and three-quarters inches in diameter.

The volume capacity of the donor chamber was approximately 20 milliliters and that of the receiving chamber was approximately 3.5 milliliters. The donor chamber was also provided with a vent and a therapeutic agent injection port sealed with a puncturable latex rubber membrane, and the receiving chamber was adapted to receive and deliver infusion liquid as generally shown in FIG. 2.

In one evaluation for unidirectional delivery from the device, ionized physiologically tolerable liquid was introduced to the receiving chamber by connecting the inlet to tubing leading to an infusion source and was allowed to move through the chamber to the outlet by connecting the outlet to a delivery tube. No liquid passed through to the empty donor chamber.

In a second evaluation, an ionized therapeutic agent, such as an antibiotic drug, was introduced into the donor chamber and the receiving chamber was maintained empty. No drug passed through to the empty receiving chamber.

In a third evaluation, liquid was introduced to the receiving chamber and drug was introduced to the donor chamber as described above. The drug electrostatically diffused unidirectionally through the rate-controlling electret membrane to the receiving chamber when the liquid in the receiving chamber was allowed to flow, but not when this flow was interrupted.

In a separate evaluation, a similar device was made using the same polymer matrix as supplied. However unlike the electret membrane above, liquids flowed bidirectionally through these membranes uninterrupted as expected.

EXAMPLE 2

This example illustrates the controlled infusion delivery of a pre-determined amount of an injectable drug in an administration protocol using the principles of this invention as embodied in the device prepared according to Example 1.

A series of 53 drugs were obtained from commercial suppliers in the usual predetermined adult single unit dosage from (typically 500 to 1000 milligrams of an antibiotic, for example). The time period for infusing at least 95 percent of the drug in a typical administration protocol was determined for that selected drug using a small volume parenteral (SVP) dilution unit as described below.

The receiving chamber of the device was primed by purging it of air with primary fluid, such as saline solution (0.9 percent NaCl in sterile water) or dextrose (5 percent in water). The flow rate from the receiving chamber was then adjusted to deliver effluent fluid at a rate of about 1.5 to about 2.0 milliliters (ml) per minute. A fluid dosage unit of 10 to 20 ml of a selected drug was introduced to the donor chamber. If the drug was not supplied in liquid form, the manufacturer's recommendation for reconstituting the single unit dose with the appropriate diluent to the desired volume. Typically an SVP dilution volume used is about 2 ml to about 20 ml.

The actual time to deliver the selected drug was monitored by collecting a sample of 50 microliters of effluent every 5 minutes in a fraction collector (Haake Buckler LC 100) until the donor chamber was substantially empty. The drug content in each of the collected fractions was analyzed by High Performance Liquid Chromatography (HPLC) method and the Percentage of Drug Recovery calculated.

For HPLC analysis, the instrumentation was a Waters Associates HPLC automatic system consisting of a Four Solvent Automatic Delivery Pumping System (Waters model 600), Waters' autosampler model 712 WISP, and Waters' model 990 photodiode array detector capable of detecting and scanning wavelengths from 190–600 nanometers. The analog signal was interpreted and analyzed by a NEC Computer model APC-III equipped with a Waters graphic plotter.

Fifty three injectable drugs, identified by common name in the table below, were delivered and monitored. The drugs included three aminoglycoside type antibiotics, one antifungal antibiotic (Miconazole); twelve cephalosporins, three beta-lactam antibiotics, two erythromycins, eight penicillins, three miscellaneous antibiotics, eleven antineoplastic agents, five cardiovascular drugs and five analgesics and antipyretics.

For analysis, the following seven different HPLC columns were used depending on the drug being analyzed as identified under the "column" heading of the table below, for each drug.

Column 1: Whatman C18, 25 cm long, 10 micron
Column 2: Alltech Versapack C18, 25 cm, 10 micron
Column 3: Waters MicroBondapack C18, 25 cm, 10 micron
Column 4: Alltech Cation Exchange, 25 cm, 10 micron
Column 5: DuPont Zorbax C18, 25 cm, 5 micron
Column 6: Lichrosorb SI, 12 cm, 5 micron
Column 7: Partisil C8, 25 cm, 10 micron Additionally the following eleven (A–K) mobile phases were used depending on the drug and these are identified by alphabetical letter under the "M. Phase" heading of the table below for each drug.

M. Phase A: 80% Acetonitrile (ACN) to 20% water
M. Phase B: 0.035 Molar (M) 65% ACN+35% Tetraethylamine acetate (TEAC), pH 4.5
M. Phase C: 0.035M 80% ACN+30% TEAC, pH 4.5
M. Phase D: 0.035M 100% TEAC, pH 4.5
M. Phase E: 0.035M 100% TEAC, pH 7.0
M. Phase F: 0.035M 60% ACN+40% TEAC, pH 4.5
M. Phase G: 0.2M 55% ACN+10% methanol+35% ammonium acetate
M. Phase H: 100% sodium sulfate
M. Phase I: 10% ammonium acetate+water+methanol+ethanol (5:19:60:46)
M. Phase J: 90% methylene chloride+9% methanol+0.1% of 25% ammonium hydroxide
M. Phase K: 30% methanol+20% 2M ammonium hydroxide+10% 1M ammonium nitrate+water The results of the analysis for each of the 53 drugs shown in the table below include the flow rate (F. Rate) of the solvent mixture pumped in the HPLC analysis, the retention time (R. Time) of the peak detected in the HPLC chromatogram, the usual adult dosage in milligrams (Dose mg) employed, the starting SVP dilution in ml placed in the donor chamber, and the infusion duration time in minutes to recover at least 95 percent of starting volume.

Percentage of Recovery (% R) was calculated as (Mi/Ms)×100, where Mi=total amount of drug collected in the combined samples and MS=is the total starting amount of drug. The amount of drug collected was calculated from the HPLC analysis of each sample Mi, where i=1, 2, 3 . . . number of samples. Mi=concentration (Ci)×volume of each sample (Vi) and Ci=Cs×Pi/Ps, where Cs is the concentration of the standard drug solution, Pi is the peak area of the sample solution and Ps is the peak area of the standard solution.

The characteristics of the drugs shown in the following table can generally be found in the pharmaceutical literature. One example of such literature is the *Merck Index Tenth Edition* published by Merck & Co., Inc., Rahway, N.J. (1986).

|  | Column | M. Phase | F. Rate ml/min | R. Time min. | Dose mg | SVP dilut ml | Infusion time-min. | % Recovery |
|---|---|---|---|---|---|---|---|---|
| Antibiotics: |  |  |  |  |  |  |  |  |
| Aminoglycosides |  |  |  |  |  |  |  |  |
| Amikacin | 3 | C | 2.0 | 1.8 | 500 | 10 | 45 | 96.3 |

-continued

| | Column | M. Phase | F. Rate ml/min | R. Time min. | Dose mg | SVP dilut ml | Infusion time-min. | % Recovery |
|---|---|---|---|---|---|---|---|---|
| Gentamicin | 1 | A | 1.5 | 3.3 | 80 | 10 | 30 | 97.5 |
| Netilmicin | 2 | A | 1.2 | 1.9 | 80 | 10 | 43 | 97.0 |
| Miconazole | 3 | A | 2.0 | 2.7 | 1000 | 10 | 47 | 95.6 |
| Cephalosporin | | | | | | | | |
| Cefamandole | 2 | E | 1.2 | 2.1 | 500 | 10 | 35 | 98.3 |
| Cefazolin | 2 | B | 1.5 | 1.8 | 500 | 10 | 40 | 96.8 |
| Cefonicid | 2 | B | 1.5 | 2.5 | 500 | 10 | 40 | 97.3 |
| Cefoperazone | 1 | A | 2.5 | 2.5 | 1000 | 10 | 35 | 95.7 |
| Ceforanide | 3 | B | 1.5 | 3.8 | 1000 | 10 | 40 | 98.0 |
| Cefotaxime | 2 | D | 1.5 | 3.4 | 1000 | 10 | 45 | 95.8 |
| Ceftizoxime | 2 | D | 1.5 | 3.0 | 1000 | 10 | 45 | 96.3 |
| Ceftriaxone | 2 | D | 1.5 | 3.9 | 250 | 10 | 40 | 98.2 |
| Cefuroxime | 2 | D | 1.5 | 2.6 | 500 | 10 | 33 | 97.3 |
| Cephalothin | 1 | B | 2.0 | 4.5 | 1000 | 10 | 45 | 96.7 |
| Cephapirin | 1 | B | 2.0 | 3.3 | 1000 | 10 | 45 | 95.2 |
| Cephradine | 2 | B | 1.5 | 2.3 | 1000 | 10 | 35 | 98.6 |
| B-Lactam Antibiotics | | | | | | | | |
| Amdinocillin | 5 | G | 1.5 | 4.2 | 500 | 10 | 45 | 95.8 |
| Cefoxitin | 5 | G | 2.0 | 5.4 | 1000 | 10 | 35 | 98.3 |
| Moxalactam | 2 | D | 2.2 | 6.8 | 1000 | 10 | 40 | 95.2 |
| Erythromycins | | | | | | | | |
| Erythromycin Ethyl. | 3 | H | 1.2 | 3.7 | 250 | 20 | 55 | 98.8 |
| Erythromycin Lact. | 3 | H | 1.2 | 3.9 | 500 | 20 | 50 | 98.2 |
| Pennicillins | | | | | | | | |
| Pennicillin G | 2 | G | 1.5 | 2.3 | 1 MM U | 20 | 50 | 97.8 |
| Methicillin | 2 | G | 1.5 | 4.2 | 1000 | 10 | 40 | 95.7 |
| Nafcillin | 2 | G | 1.5 | 3.9 | 500 | 10 | 43 | 98.9 |
| Oxacillin | 2 | G | 2.0 | 4.7 | 500 | 10 | 40 | 96.1 |
| Ampicillin | 2 | G | 1.8 | 2.8 | 250 | 10 | 45 | 95.9 |
| Carbenicillin | 2 | G | 1.5 | 2.5 | 1000 | 10 | 35 | 98.8 |
| Piperacillin | 2 | G | 1.5 | 2.1 | 2000 | 10 | 33 | 100.5 |
| Ticarcillin | 2 | G | 1.5 | 5.3 | 1000 | 10 | 50 | 97.3 |
| Miscellaneous | | | | | | | | |
| Clindamycin | 3 | G | 1.5 | 3.8 | 600 | 10 | 35 | 96.8 |
| Lincomycin | 3 | G | 1.5 | 2.9 | 600 | 10 | 37 | 97.7 |
| Vancomycin | 2 | B | 2.0 | 5.3 | 1000 | 10 | 65 | 98.8 |
| Antincoplastic | | | | | | | | |
| Bleomycin | 6 | I | 2.0 | 7.5 | 25 U | 10 | 65 | 97.2 |
| Carmustine | 6 | I | 2.0 | 3.8 | 200 | 10 | 45 | 98.3 |
| Cyclophosphamide | 4 | G | 1.5 | 4.7 | 150 | 10 | 38 | 96.9 |
| Cytarabine | 4 | F | 1.5 | 3.3 | 150 | 10 | 45 | 97.9 |
| Dacarbazine | 4 | F | 1.5 | 5.2 | 300 | 10 | 63 | 95.9 |
| Daunorubicin | 5 | J | 1.5 | 5.8 | 50 | 10 | 65 | 95.6 |
| Doxorubicin | 5 | J | 1.5 | 4.7 | 50 | 10 | 57 | 97.8 |
| Fluorouracil | 5 | J | 2.0 | 5.3 | 150 | 10 | 45 | 98.5 |
| Mechlorethamine | 2 | G | 1.2 | 3.8 | 10 | 10 | 40 | 97.8 |
| Methotrexate | 2 | B | 1.5 | 4.7 | 20 | 20 | 45 | 98.9 |
| Mitomycin | 2 | G | 2.0 | 5.8 | 20 | 20 | 63 | 95.8 |
| Cardiovascular | | | | | | | | |
| Procaine | 2 | B | 1.5 | 3.9 | 500 | 10 | 60 | 96.7 |
| Verapamil | 2 | B | 1.5 | 2.5 | 10 | 10 | 47 | 98.3 |
| Amrimone Lactate | 3 | G | 2.0 | 4.7 | 10 | 10 | 40 | 97.2 |
| Procainamide | 2 | B | 1.5 | 1.9 | 500 | 10 | 44 | 98.8 |
| Quinidine gluconate | 2 | G | 1.5 | 4.8 | 800 | 10 | 57 | 96.7 |
| Analgesics and Antipyretics | | | | | | | | |
| Chloroprocaine | 2 | B | 1.5 | 3.2 | 100 | 10 | 37 | 99.1 |
| Bupivacaine | 1 | F | 2.0 | 2.8 | 175 | 10 | 35 | 97.8 |
| Meperidine | 1 | F | 2.0 | 5.2 | 35 | 10 | 65 | 95.8 |
| Morphine Sulphate | 7 | K | 2.0 | 4.5 | 10 | 20 | 35 | 98.9 |
| Fentanyl Citrate | 7 | K | 2.0 | 5.1 | 100 | 10 | 55 | 96.3 |

The results show that the delivery of the drugs under the principles of this invention using the rate-controlling electret membrane and device satisfactorily administered the drugs in an administration protocol of from about 30 to about 60 minutes. Such a controlled drug delivery is very important and desirable especially when cardiovascular drugs are administered.

EXAMPLE 3

This example illustrates the electrostatic diffusion pattern for drug delivery obtained by the procedure in Example 2 with the device of this invention compared against that of three traditionally safe secondary administration techniques. A dosage of 1000 milligrams of Cephalothin (a sodium salt of cephalosporin antibiotic) was delivered over a period of about 40 to about 60 minutes.

For comparison, the pattern of delivery was analyzed for the same adult dosage of this drug administered by conventional intravenous (IV) push, by a commercial infusion system marketed by the IVAC Corporation under the trade designation CRIS, and by a conventional minibag technique. These results are graphically summarized and compared in FIG. 8.

EXAMPLE 4

The comparative procedure of Example 3 was repeated except that the drug was an aminoglycoside type antibiotic, Vancomycin Hydrochloride delivered at a dosage of 500 milligram. These results are graphically summarized and compared in FIG. 9.

EXAMPLE 5

Figure 10:
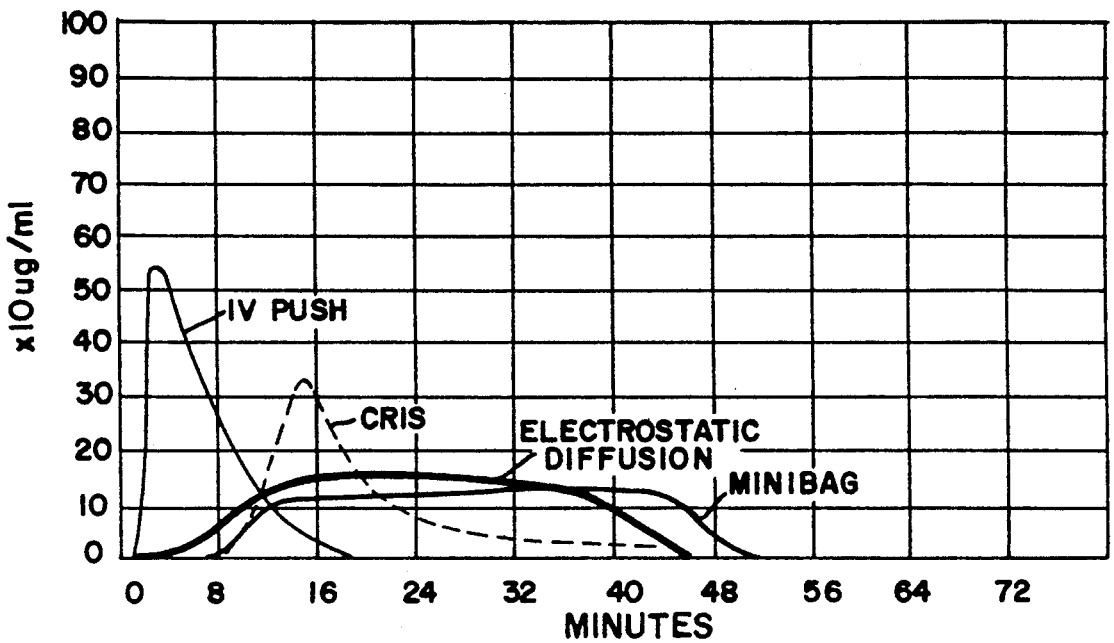

The comparative procedure of Example 3 was repeated except that the drug was Verapamil Hydrochloride, a cardiovascular drug delivered at a dosage of 10 milligrams. These results are summarized and compared in FIG. 10.

EXAMPLE 6

Figure 11:
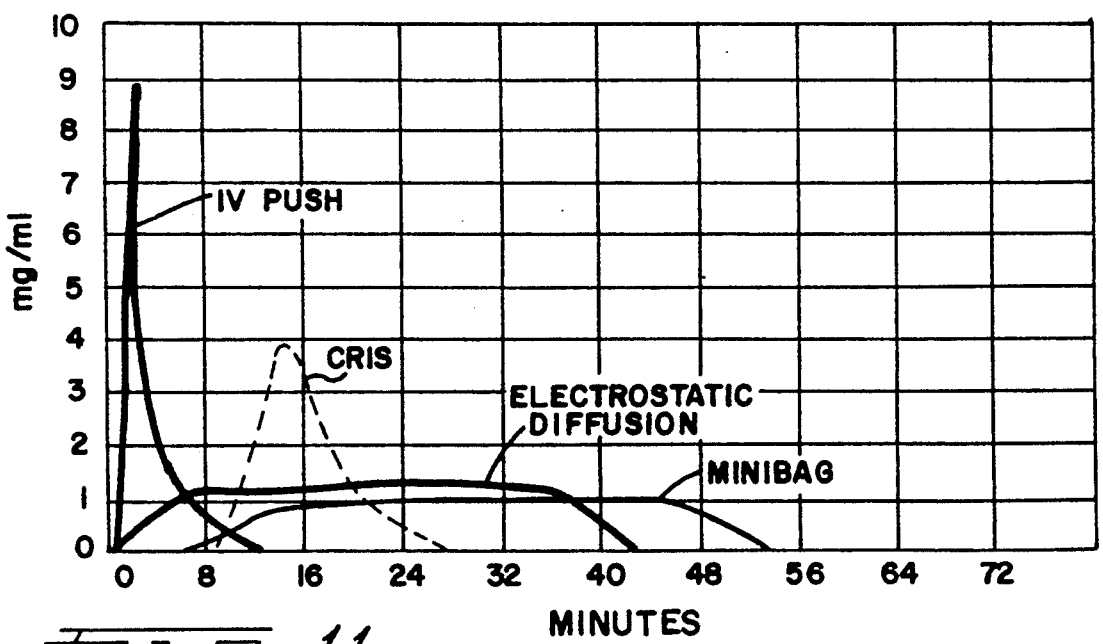

The comparative procedure of Example 3 was repeated, except that the drug was Doxorubicin Hydrochloride, an antineoplastic drug, delivered at a dosage of 50 milligrams. These results are summarized and compared in FIG. 11.

EXAMPLE 7

Figure 12:
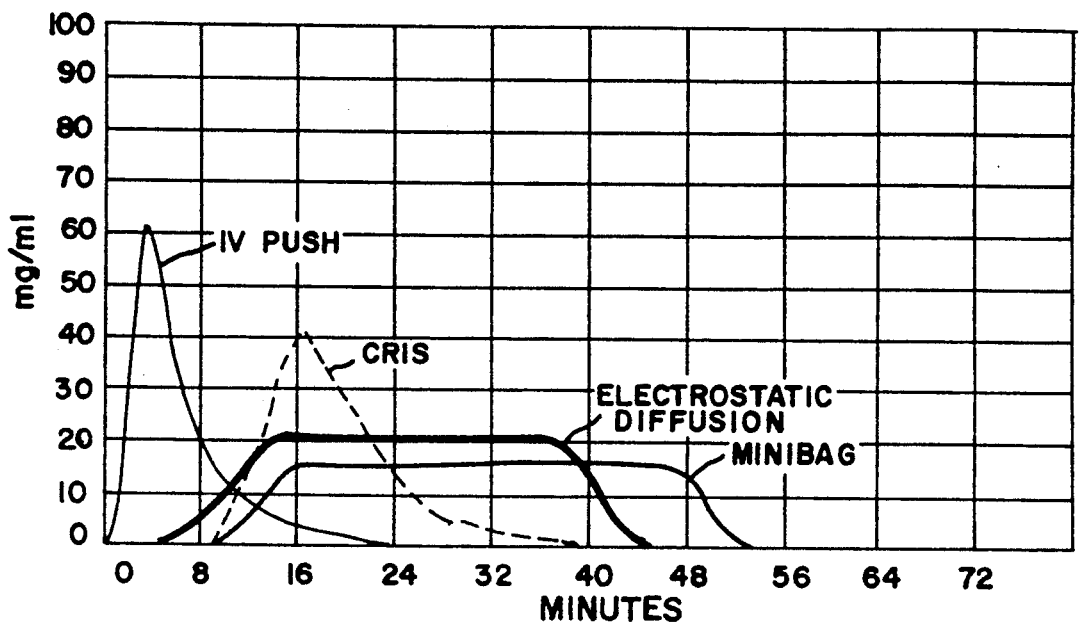

The comparative procedure of Example 3 was repeated, except that the drug was Nafcillin sodium, a penicillin antibiotic delivered at a 500 milligrams dosage over a period of 30 to 60 minutes. These results are summarized and compared in FIG. 12.

EXAMPLE 8

Figure 13:
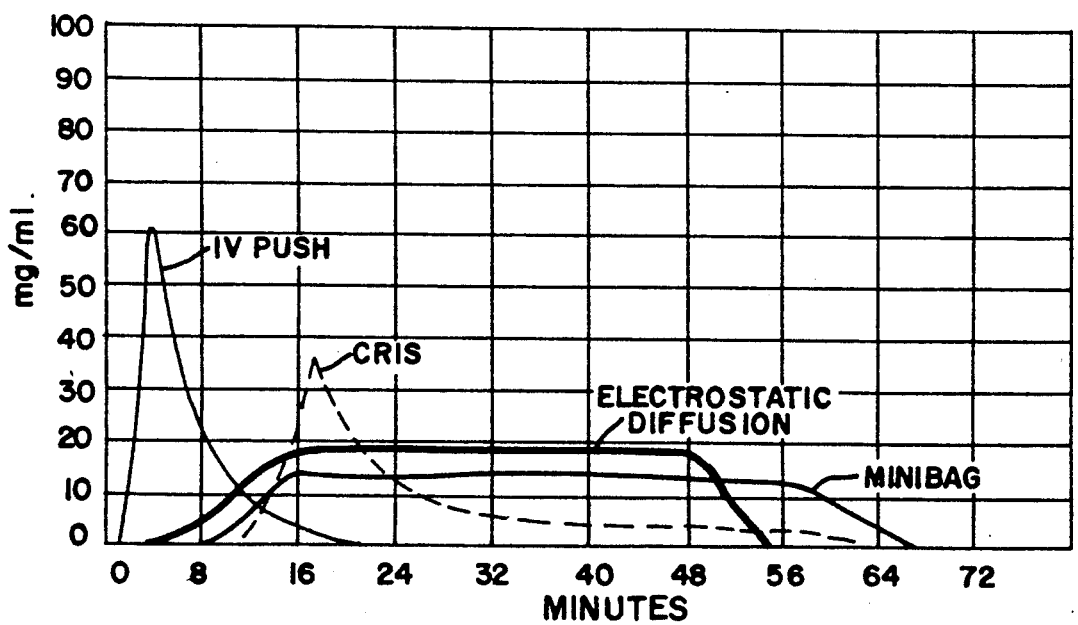

The comparative procedure of Example 3 was repeated, excepted that the drug was Erythromycin Lactobionate delivered at a dosage of 500 milligrams. These results are summarized and compared in FIG. 13.

In the foregoing Examples 3-8, the pattern of drug delivery from the device of this invention was judged satisfactory with a profile of delivery generally falling between that of the minibag and the CRIS systems.

It will be understood that various changes and modifications can be made in the above-described embodiments of this invention without departing from the spirit thereof and that no limitation with respect to the specific embodiments described and illustrated is intended or should be inferred.

What is claimed is:

1. A method of preparing an electret membrane comprising a polyelectrolyte salt and a porous hydrophilic polymer matrix having a charge modified ionic surface comprising the steps of:
   providing the polymer matrix;
   providing a solution of polyelectrolyte salt;
   impregnating the polymer matrix by immersion in the polyelectrolyte solution;
   elevating the temperature of the polyelectrolyte solution;
   maintaining the immersed polymer matrix at the elevated temperature to form an electret membrane; and
   drying the electret membrane.

2. The membrane formed by the method of claim 1.

3. The method of claim 1 wherein the polyelectrolyte is sodium polystyrene sulfonate.

4. The method of claim 1 wherein the polymer matrix comprises a modified Nylon film having amine groups and carboxyl groups on its surface.

5. An electret membrane comprised of a charge modified Nylon film having 50 percent amine groups and 50 percent carboxyl groups on its surface and impregnated with sodium polystyrene sulfonate by the method of claim 3.

* * * * *